(12) United States Patent
Fukushima et al.

(10) Patent No.: US 10,088,396 B2
(45) Date of Patent: *Oct. 2, 2018

(54) FLUORINE-CONTAINING BORIC ACID COMPOSITE CAPSULE PARTICLES

(71) Applicants: UNIMATEC CO., LTD., Tokyo (JP); HIROSAKI UNIVERSITY, Aomori (JP)

(72) Inventors: Takeshi Fukushima, Ibaraki (JP); Katsuyuki Sato, Ibaraki (JP); Hideo Sawada, Aomori (JP)

(73) Assignees: Unimatec Co., Ltd., Tokyo (JP); Hirosaki University, Aomori (JP)

( * ) Notice: Subject to any disclaimer, the term of this patent is extended or adjusted under 35 U.S.C. 154(b) by 12 days.

This patent is subject to a terminal disclaimer.

(21) Appl. No.: 15/125,045

(22) PCT Filed: Mar. 10, 2015

(86) PCT No.: PCT/JP2015/057025
§ 371 (c)(1),
(2) Date: Sep. 9, 2016

(87) PCT Pub. No.: WO2015/137346
PCT Pub. Date: Sep. 17, 2015

(65) Prior Publication Data
US 2017/0023448 A1    Jan. 26, 2017

(30) Foreign Application Priority Data

Mar. 11, 2014  (JP) ................. 2014-047316

(51) Int. Cl.
| | | |
|---|---|---|
| *C09D 5/16* | (2006.01) | |
| *C09D 201/00* | (2006.01) | |
| *C08K 5/55* | (2006.01) | |
| *C08L 101/00* | (2006.01) | |
| *C03C 17/00* | (2006.01) | |
| *C09D 7/40* | (2018.01) | |
| *C08K 9/10* | (2006.01) | |
| *G01N 1/30* | (2006.01) | |
| *C07C 41/26* | (2006.01) | |
| *C07C 43/13* | (2006.01) | |

(52) U.S. Cl.
CPC .......... *G01N 1/30* (2013.01); *C07C 41/26* (2013.01); *C07C 43/137* (2013.01); *C08K 9/10* (2013.01); *C09D 5/16* (2013.01); *G01N 2001/302* (2013.01)

(58) Field of Classification Search
CPC ...... C09D 7/12; C09D 201/00; C09D 5/1625; C09D 5/1668; C09D 5/1681; C08K 5/55; C08L 101/00; C03C 17/009; C03C 2217/76; C03C 2218/111
See application file for complete search history.

(56) References Cited

U.S. PATENT DOCUMENTS

| | | | |
|---|---|---|---|
| 3,574,770 A | 4/1971 | Paine | |
| 9,475,826 B2 * | 10/2016 | Sato | ............... C08G 77/18 |
| 2009/0036706 A1* | 2/2009 | Murata | ............... C07C 17/275 |
| | | | 560/227 |
| 2009/0143621 A1* | 6/2009 | Martin | ............... C07C 41/03 |
| | | | 564/96 |
| 2009/0171127 A1 | 7/2009 | Murata et al. | |
| 2016/0009739 A1* | 1/2016 | Sato | ............... C07C 29/149 |
| | | | 556/470 |

FOREIGN PATENT DOCUMENTS

| | | |
|---|---|---|
| GB | 2 274 661 A | 8/1994 |
| JP | 05-186719 | 7/1993 |
| JP | H6-294097 | 10/1994 |
| JP | 2004-285111 | 10/2004 |

(Continued)

OTHER PUBLICATIONS

International Search Report from corresponding PCT application No. PCT/JP2015/057024 dated Apr. 14, 2015 (4 pgs).

Natsuki Jin et al., "Gan Fusso Alcohol/Hosan/Guest Bunshi Nanocomposite no Chosei to Seishitsu", CSJ: The Chemical Society of Japan Koen Yokoshu, 94$^{th}$, 3, p. 1003, 3PA-125.

Natsuki Jin et al., "Gan Fusso Alcohol/Hosan Nanocomposite-rui no Chosei to Oyo", Polymer Preprints, Japan, vol. 63, No. 1, pp. 2703-2704, 3Pb084.

Takuto Shimamura et al., "Fluoroalkyl Group Gan'yu Oligomer/ Hosan/Silica Nanocomposite-rui no Chosei to Tainetsusei", Japan Society of Colour Material Conference Koen Yoshishu, 2013, pp. 188-189, P17.

(Continued)

*Primary Examiner* — Blessing M Fubara
(74) *Attorney, Agent, or Firm* — Brinks Gilson & Lione

(57) ABSTRACT

Fluorine-containing boric acid composite capsule particles comprising a condensate of a fluorine-containing alcohol, a guest compound, and boric acid particles, wherein the fluorine-containing alcohol is represented by the general formula:

$$R_F\text{-A-OH}$$

wherein $R_F$ is:
a perfluoroalkyl group having 6 or less carbon atoms,
a linear or branched perfluoroalkyl group containing a terminal perfluoroalkyl group having 6 or less carbon atoms and a perfluoroalkylene group having 6 or less carbon atoms, and containing an O, S, or N atom, or
a polyfluoroalkyl group in which some of the fluorine atom or atoms of the perfluoroalkyl group are replaced by hydrogen atom or atoms, and which contains a terminal perfluoroalkyl group having 6 or less carbon atoms and a perfluoroalkylene group having 6 or less carbon atoms, wherein the perfluoroalkylene group may contain an O, S, or N atom, and one fluorine atom of the terminal perfluoroalkyl group may be replaced by —$(CH_2)_f$OH (wherein f is an integer of 1 to 3); and
A is an alkylene group having 1 to 6 carbon atoms.

8 Claims, 5 Drawing Sheets

(56) References Cited

FOREIGN PATENT DOCUMENTS

| JP | 2007-213993 | 8/2007 |
|---|---|---|
| JP | 2007-277516 | 10/2007 |
| JP | 2008-038015 | 2/2008 |
| JP | 2008-098687 | 4/2008 |
| JP | 2009-073799 | 4/2009 |
| JP | 2010-138156 | 6/2010 |
| JP | 4674604 | 2/2011 |
| JP | 2012-188635 | 10/2012 |
| JP | 2014-196482 | 10/2014 |
| WO | WO 2007/080949 A1 | 7/2007 |

OTHER PUBLICATIONS

Takuto Shimamura et al., "Gan Fusso Oligomer/Hoso Nanocomposite no Chosei to Seishitsu", CSJ: The Chemical Society of Japan Koen Yokoshu, 2013, $93^{rd}$, 3, p. 1070, PC-112.

International Preliminary Report on Patentability and Written Opinion from corresponding PCT application No. PCT/JP2015/057025 dated Sep. 22, 2016 (5 pgs).

* cited by examiner

[Fig. 1]
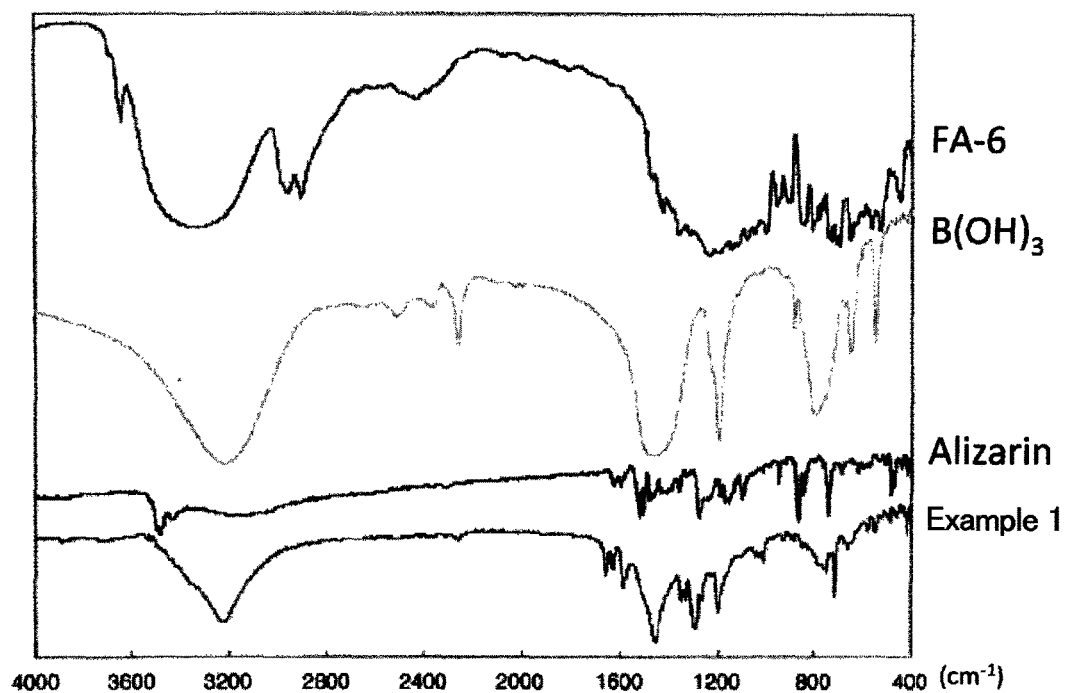

[Fig. 2]
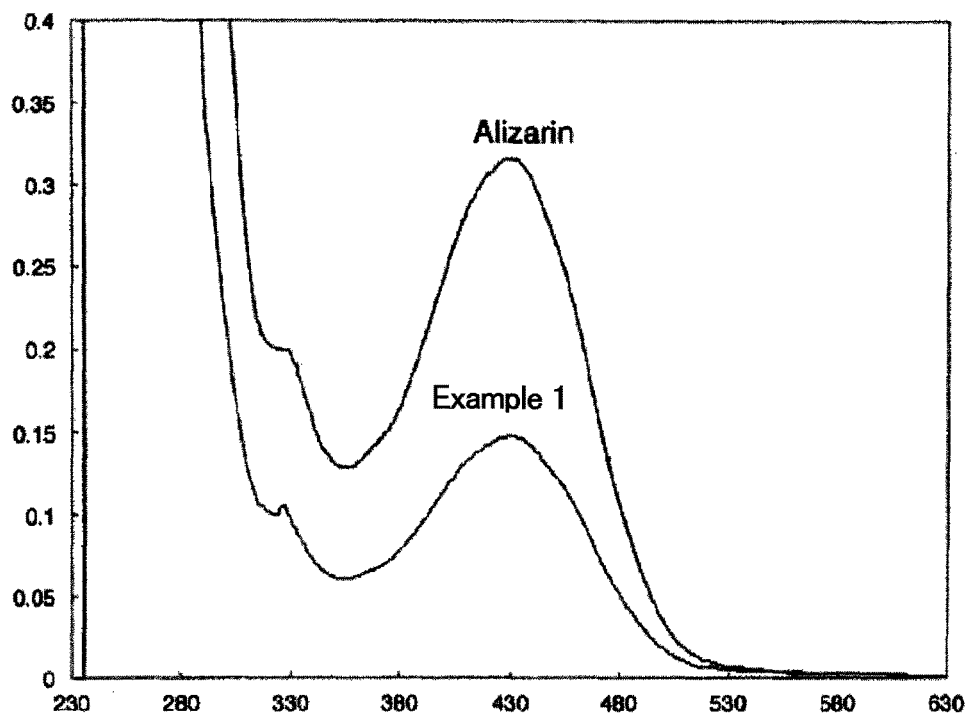
[Fig. 3]
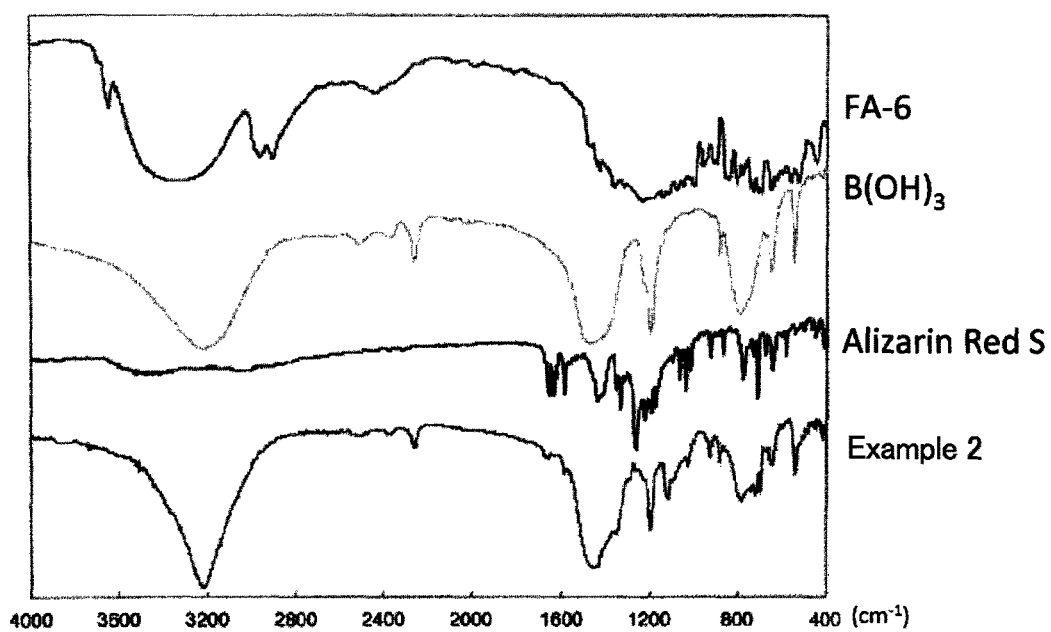

[Fig. 4]
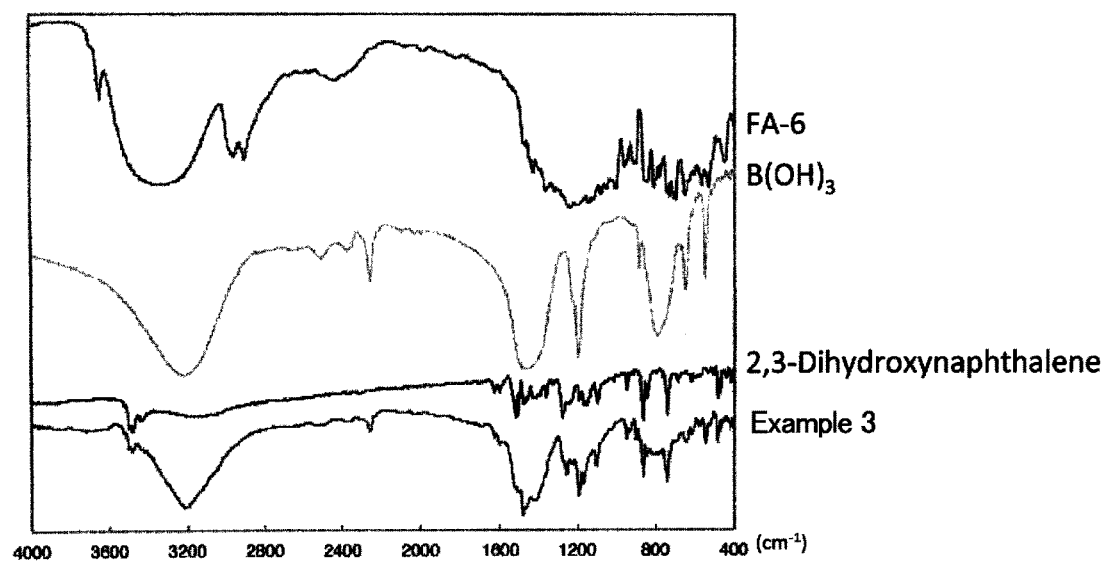
[Fig. 5]
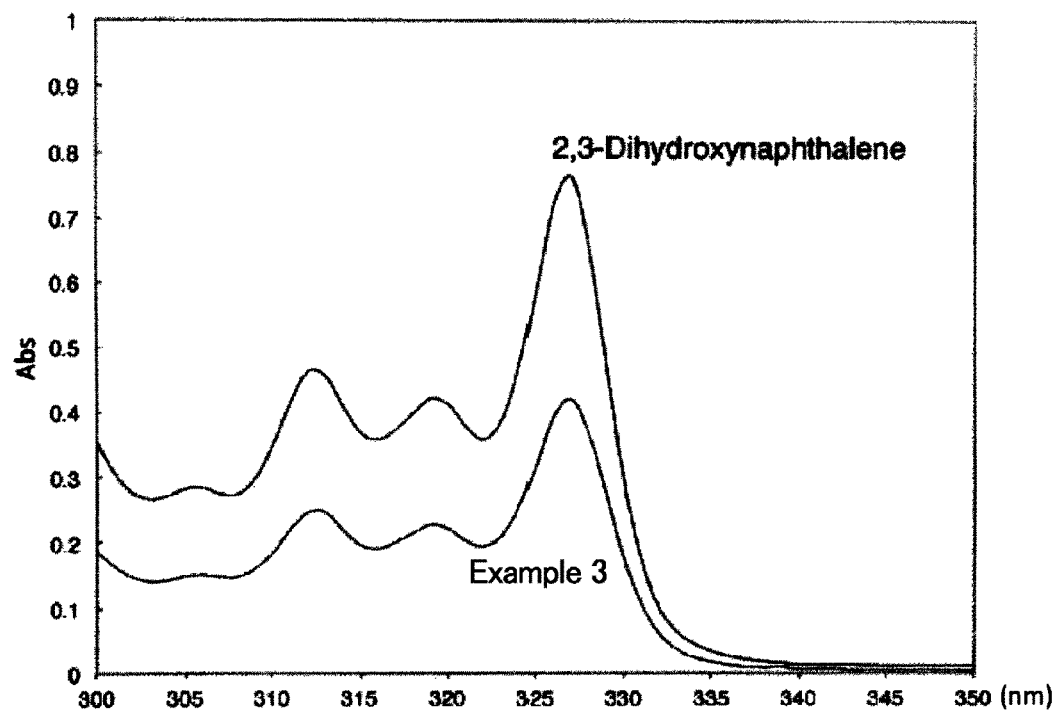

[Fig. 6]
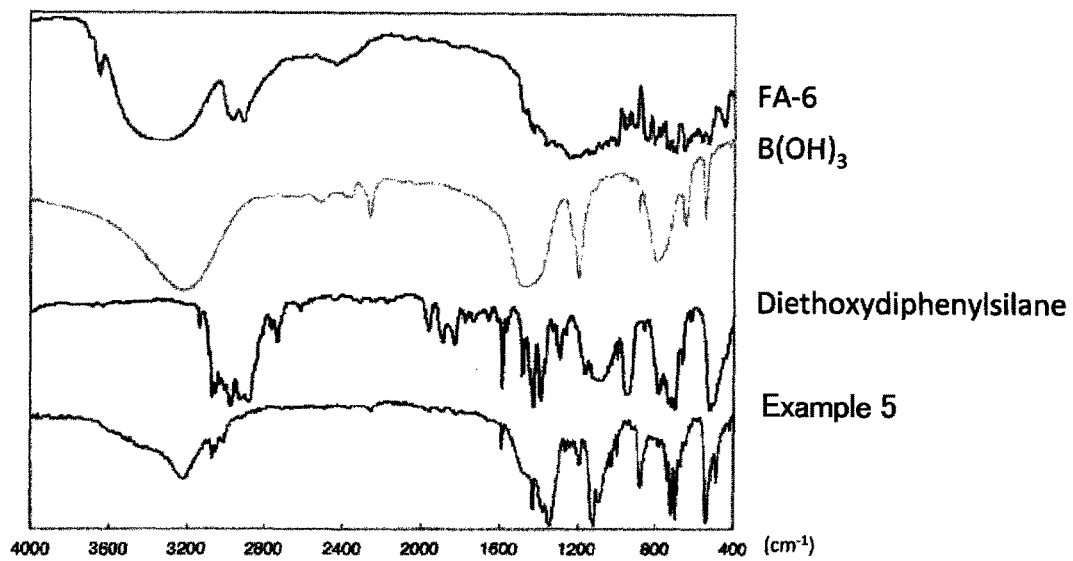
[Fig. 7]
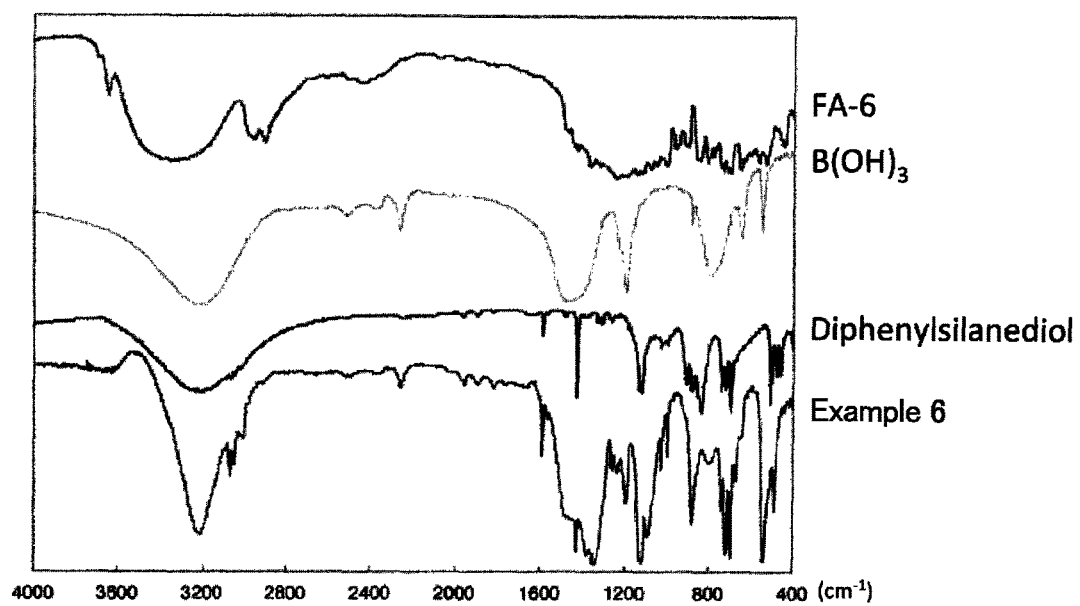

[Fig. 8]
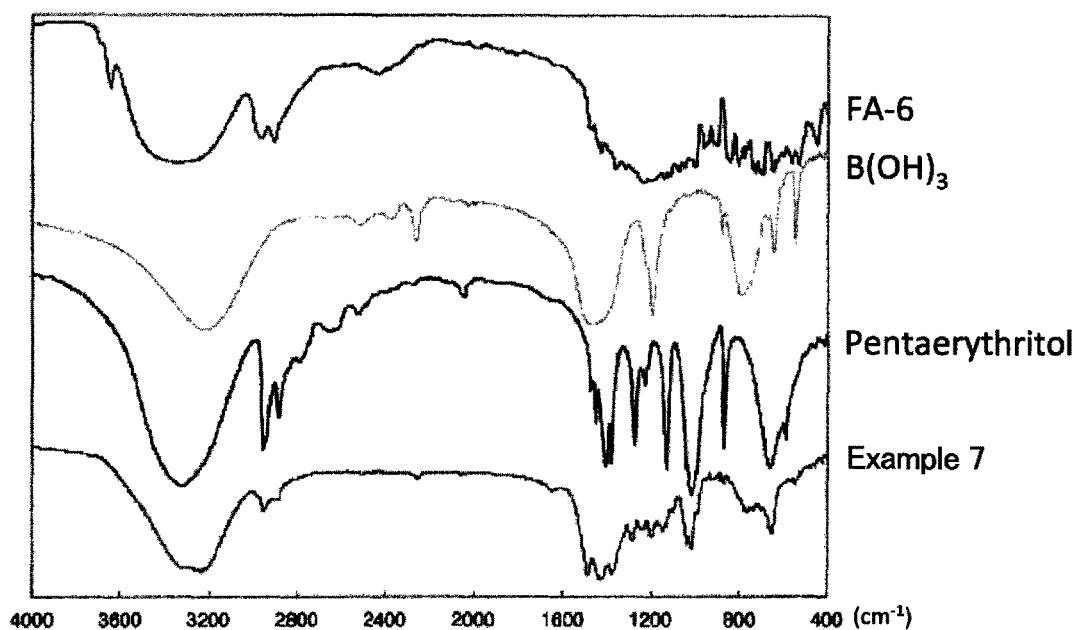

FLUORINE-CONTAINING BORIC ACID COMPOSITE CAPSULE PARTICLES

RELATED APPLICATION

This application is a 35 U.S.C. § 371 national phase filing of International Patent Application No. PCT/JP2015/057025, filed Mar. 10, 2015, which claims priority under 35 U.S.C. § 119 to Japanese Patent Application No. 2014-047316, filed Mar. 11, 2014, the entire disclosure of which is hereby expressly incorporated by reference.

TECHNICAL FIELD

The present invention relates to fluorine-containing boric acid composite capsule particles. More particularly, the present invention relates to fluorine-containing boric acid composite capsule particles in which a guest compound is clathrated.

BACKGROUND ART

Boron atoms (B) have an empty p-orbital; therefore, boron compounds act as Lewis acids and are applied to various organic synthesis reactions. In particular, boron compounds in which a fluorine atom or hexafluorobenzene is bound to a boron atom are known to exhibit very strong Lewis acidity by the action of the fluorine atom. Accordingly, boronic acid salts can be easily formed by reacting a boron compound with a Lewis base, such as an alcohol or an amine compound.

Organic compounds having a fluorescent chromophore (fluorescent compounds) are less expensive than fluorescent inorganic compounds, and are thus used as fluorescent ink or pigment for various applications, including coloring agents for resin, fiber, etc. Specifically, fluorescent compounds having a reactive substituent are used as fluorescent tags for bio-imaging. Moreover, a fluorescent compound can also be used in the luminescent layer of an organic electroluminescence element. In a color-conversion type-organic electroluminescence element, a fluorescent compound is used in a color filter (Patent Document 1). Furthermore, a fluorescent compound is also used to adjust the color tone and brightness of a light emitting diode (Patent Document 2). The term "fluorescent" used herein means that fluorescence is emitted by light irradiation at room temperature.

In addition to typical fluorescent compounds, such as rhodamine, fluorescein, and cyanine, some of compounds with a simple structure, such as coumarin and quinoline, exhibit strong fluorescence. For example, coumarin derivatives are used as fluorescent whitening agents for fiber and paper (Patent Document 3).

It is known that various surface characteristics are developed by coating inorganic material surfaces with various compounds or polymers. In particular, when a fluorine-based compound is used for surface treatment, surface modification can be applied for not only water-repellency, but also oil-repellency, due to characteristics of fluorine atoms. Thus, such fluorine-based compounds are used for coating on various substrates.

In particular, coating showing highly water- and oil-repellency can be obtained by applying a surface-treating agent having a $C_8$ perfluoroalkyl group to substrates. However, it is recently reported that compounds containing a perfluoroalkyl group having 7 or more carbon atoms induce intracellular communication inhibition, which is considered to be a carcinogenic factor, in in-vitro tests using cell strains; that this inhibition depends on the length of the fluorinated carbon chain, rather than the functional groups; and that a longer carbon chain has higher inhibitory actively. The production of monomers using fluorinated long-carbon-chain compounds has been restricted.

Patent Documents 4 and 5 indicate that a fluorine-containing alcohol, an alkoxysilane (and a polymerizable functional group-containing alcohol) are subjected to a condensation reaction. However, the resulting alkoxysilane derivatives are used for the preparation of a curable composition to which a photoacid generator or photobase generator is added, or for the preparation of an inorganic conductive coating composition.

PRIOR ART DOCUMENTS

Patent Documents

Patent Document 1: JP-A-2007-213993
Patent Document 2: JP-A-2008-98687
Patent Document 3: JP-A-6-294097
Patent Document 4: JP-A-2004-285111
Patent Document 5: JP-A-5-186719
Patent Document 6: JP-B-4674604
Patent Document 7: WO 2007/080949 A1
Patent Document 8: JP-A-2008-38015
Patent Document 9: U.S. Pat. No. 3,574,770

OUTLINE OF THE INVENTION

Problem to be Solved by the Invention

An object of the present invention is to provide fluorine-containing boric acid composite capsule particles that do not produce perfluorooctanoic acid, etc., even when released into the environment, that use a fluorine-containing alcohol having units easily degradable to short-chain compounds, and that encapsulate a fluorescent compound, which is used as a guest compound, to thereby allow the particles to exhibit fluorescence characteristics and have characteristics derived from the fluorine-containing alcohol.

Means for Solving the Problem

The present invention provides fluorine-containing boric acid composite capsule particles comprising a condensate of a fluorine-containing alcohol, a guest compound, and boric acid particles, wherein the fluorine-containing alcohol is represented by the general formula:

$$R_F\text{-A-OH} \qquad [I]$$

wherein $R_F$ is:
  a perfluoroalkyl group having 6 or less carbon atoms,
  a linear or branched perfluoroalkyl group containing a terminal perfluoroalkyl group having 6 or less carbon atoms and a perfluoroalkylene group having 6 or less carbon atoms, and containing an O, S, or N atom, or
  a polyfluoroalkyl group in which some of the fluorine atom or atoms of the perfluoroalkyl group are replaced by hydrogen atom or atoms, and which contains a terminal perfluoroalkyl group having 6 or less carbon atoms and a perfluoroalkylene group having 6 or less carbon atoms, wherein the perfluoroalkylene group may contain an O, S, or N atom, and one fluorine atom of the terminal perfluoroalkyl group may be replaced by —(CH$_2$)$_f$OH (wherein f is an integer of 1 to 3); and A is an alkylene group having 1 to 6 carbon atoms.
The condensation reaction is performed under acidic or alkaline conditions. The number of carbon atoms is preferably 4 to 6.

The perfluoroalkylene group of the fluorine-containing alcohol represented by the above general formula [I] may be a group containing an O, S, or N atom. This fluorine-containing alcohol is represented by the general formula [IV] described later. Moreover, in the polyfluoroalkyl group, one fluorine atom of the terminal perfluoroalkyl group may be replaced by —(CH$_2$)$_f$OH (wherein f is an integer of 1 to 3). This fluorine-containing alcohol is represented by the general formula [V] described later.

Effect of the Invention

The fluorine-containing alcohols used in the present invention have a terminal perfluoroalkyl group or a perfluoroalkylene chain in a polyfluoroalkyl group, having 6 or less carbon atoms, and have units easily degradable to short-chain compounds having 6 or less carbon atoms. Therefore, they do not lead to environmental pollution. Moreover, by using a fluorescent compound or the like as the guest compound and encapsulating it, the resulting fluorine-containing boric acid composite capsule particles can exhibit fluorescence characteristics and have surface characteristics, such as water- and oil-repellency, derived from the characteristics of the fluorine-containing alcohol.

BRIEF DESCRIPTION OF DRAWINGS

FIG. 1: FT-IR of the reaction product obtained in Example 1.
FIG. 2: UV spectrum absorption curve of the reaction product obtained in Example 1.
FIG. 3: FT-IR of the reaction product obtained in Example 2.
FIG. 4: FT-IR of the reaction product obtained in Example 3.
FIG. 5: UV spectrum absorption curve of the reaction product obtained in Example 3.
FIG. 6: FT-IR of the reaction product obtained in Example 5.
FIG. 7: FT-IR of the reaction product obtained in Example 6.
FIG. 8: FT-IR of the reaction product obtained in Example 7.

EMBODIMENTS FOR CARRYING OUT THE INVENTION

The fluorine-containing alcohol [I] can be a fluorine-containing alcohol wherein the R$_F$ group is a perfluoroalkyl group having 6 or less carbon atoms, for example, a polyfluoroalkyl alcohol represented by the general formula:

$$C_nF_{2n+1}(CH_2)_j OH \qquad [II]$$

n: 1 to 6, preferably 4 to 6
j: 1 to 6, preferably 1 to 3, particularly preferably 2
The alkylene group A is, for example, a —CH$_2$— group, a —CH$_2$CH$_2$— group, or the like. Examples of the perfluoroalkyalkyl alcohols having such an alkylene group include 2,2,2-trifluoroethanol (CF$_3$CH$_2$OH), 3,3,3-trifluoropropanol (CF$_3$CH$_2$CH$_2$OH), 2,2,3,3,3-pentafluoropropanol (CF$_3$CF$_2$CH$_2$OH), 3,3,4,4,4-pentafluorobutanol (CF$_3$CF$_2$CH$_2$CH$_2$OH), 2,2,3,3,4,4,5,5,5-nonafluoropentanol (CF$_3$CF$_2$CF$_2$CF$_2$CH$_2$OH), 3,3,4,4,5,5,6,6,6-nonafluorohexanol (CF$_3$CF$_2$CF$_2$CF$_2$CH$_2$CH$_2$OH), 3,3,4,4,5,5,6,6,7,7,8,8,8-tridecafluorooctanol (CF$_3$CF$_2$CF$_2$CF$_2$CF$_2$CF$_2$CH$_2$CH$_2$OH), and the like.

Moreover, a polyfluoroalkyl group refers to a group in which the terminal —CF$_3$ group of a perfluoroalkyl group is replaced by, for example, a —CF$_2$H group or a group in which the intermediate —CF$_2$— group is replaced by a —CFH— group or a —CH$_2$— group. Examples of the fluorine-containing alcohol [I] having such a substituent include 2,2,3,3-tetrafluoropropanol (HCF$_2$CF$_2$CH$_2$OH), 2,2,3,4,4,4-hexafluorobutanol (CF$_3$CHFCF$_2$CH$_2$OH), 2,2,3,3,4,4,5,5-octafluoropentanol (HCF$_2$CF$_2$CF$_2$CF$_2$CH$_2$OH), and the like.

The polyfluoroalkyl alcohol represented by the general formula [II] is described, for example, in Patent Document 6, and is synthesized through the following series of steps.

First, a polyfluoroalkyl iodide represented by the general formula:

$$C_nF_{2n+1}(CF_2CF_2)_b(CH_2CH_2)_cI$$

is reacted with N-methylformamide HCONH(CH$_3$) to form a mixture of polyfluoroalkyl alcohol and its formate. Then, the mixture is subjected to a hydrolysis reaction in the presence of an acid catalyst to form a polyfluoroalkyl alcohol of the formula:

$$C_nF_{2n+1}(CF_2CF_2)_b(CH_2CH_2)_cOH$$

However, the value of n+2b is 6 or less.
Examples of the polyfluoroalkyl iodide include the following:

CF$_3$(CH$_2$CH$_2$)I
CF$_3$(CH$_2$CH$_2$)$_2$I
C$_2$F$_5$(CH$_2$CH$_2$)I
C$_2$F$_5$(CH$_2$CH$_2$)$_2$I
C$_3$F$_7$(CH$_2$CH$_2$)I
C$_3$F$_7$(CH$_2$CH$_2$)$_2$I
C$_4$F$_9$(CH$_2$CH$_2$)I
C$_4$F$_9$(CH$_2$CH$_2$)$_2$I
C$_2$F$_5$(CF$_2$CF$_2$)(CH$_2$CH$_2$)I
C$_2$F$_5$(CF$_2$CF$_2$)(CH$_2$CH$_2$)$_2$I
C$_2$F$_5$(CF$_2$CF$_2$)$_2$(CH$_2$CH$_2$)I
C$_2$F$_5$(CF$_2$CF$_2$)$_2$(CH$_2$CH$_2$)$_2$I
C$_4$F$_9$(CF$_2$CF$_2$)(CH$_2$CH$_2$)I
C$_4$F$_9$(CF$_2$CF$_2$)(CH$_2$CH$_2$)$_2$I

The fluorine-containing alcohol [I] may also be a fluorine-containing alcohol wherein the R$_F$ group is a polyfluoroalkyl group in which some of the fluorine atom or atoms of the perfluoroalkyl group are replaced by hydrogen atom or atoms, and which contains a terminal perfluoroalkyl group having 6 or less carbon atoms and a perfluoroalkylene group having 6 or less carbon atoms, specifically, a polyfluoroalkyl group having 3 to 20 carbon atoms, preferably 6 to 10 carbon atoms, and A is an alkylene group having 2 to 6 carbon atoms, preferably 2 carbon atoms. Examples thereof, for example, include a polyfluoroalkyl alcohol represented by the general formula:

$$C_nF_{2n+1}(CH_2CF_2)_a(CF_2CF_2)_b(CH_2CH_2)_cOH \qquad [III]$$

n: 1 to 6, preferably 2 to 4
a: 1 to 4, preferably 1
b: 0 to 2, preferably 1 or 2
c: 1 to 3, preferably 1
The polyfluoroalkyl alcohol represented by the general formula [III] is disclosed in Patent Document 6, and synthesized through the following series of steps.

First, a polyfluoroalkyl iodide represented by the general formula:

$$C_nF_{2n+1}(CH_2CF_2)_a(CF_2CF_2)_b(CH_2CH_2)_cI$$

is reacted with N-methylformamide $HCONH(CH_3)$ to form a mixture of polyfluoroalkyl alcohol and its formate. The mixture is then subjected to a hydrolysis reaction in the presence of an acid catalyst to form a polyfluoroalkyl alcohol of the formula:

$$C_nF_{2n+1}(CH_2CF_2)_a(CF_2CF_2)_b(CH_2CH_2)_cOH$$

Examples of the polyfluoroalkyl iodide include the following:

$CF_3(CH_2CF_2)(CH_2CH_2)I$
$C_2F_5(CH_2CF_2)(CH_2CH_2)I$
$C_2F_5(CH_2CF_2)(CH_2CH_2)_2I$
$C_3F_7(CH_2CF_2)(CH_2CH_2)I$
$C_3F_7(CH_2CF_2)(CH_2CH_2)_2I$
$C_4F_9(CH_2CF_2)(CH_2CH_2)I$
$C_4C_9(CH_2CF_2)(CH_2CH_2)_2I$
$C_2F_5(CH_2CF_2)(CF_2CF_2)(CH_2CH_2)I$
$C_2F_5(CH_2CF_2)(CF_2CF_2)(CH_2CH_2)_2I$
$C_2F_5(CH_2CF_2)_2(CF_2CF_2)(CH_2CH_2)I$
$C_2F_5(CH_2CF_2)_2(CF_2CF_2)(CH_2CH_2)_2I$
$C_4F_9(CH_2CF_2)(CF_2CF_2)(CH_2CH_2)I$
$C_4C_9(CH_2CF_2)_2(CF_2CF_2)(CH_2CH_2)I$
$C_4F_9(CH_2CF_2)(CF_2CF_2)(CH_2CH_2)_2I$
$C_4F_9(CH_2CF_2)_2(CF_2CF_2)(CH_2CH_2)_2I$

The fluorine-containing alcohol [I] is a fluorine-containing alcohol wherein the $R_F$ group is a linear or branched perfluoroalkyl group containing an O, S, or N atom, specifically, a perfluoroalkyl group having 3 to 305 carbon atoms, preferably 8 to 35 carbon atoms, and containing O, S, or N atom, and A is an alkylene group having 1 to 3 carbon atoms, preferably 1 carbon atom. Examples thereof, for example, include a hexafluoropropene oxide oligomer alcohol represented by the general formula:

$$C_mF_{2m+1}O[CF(CF_3)CF_2O]_dCF(CF_3)(CH_2)_eOH \quad [IV]$$

m: 1 to 3, preferably 3
d: 0 to 100, preferably 1 to 10
e: 1 to 3, preferably 1

Moreover, the $R_F$ group of the fluorine-containing alcohol [I] can also contain a terminal alcohol group. Such a divalent fluorine-containing alcohol is one wherein the $R_F$ group is a linear or branched polyfluoroalkylene group containing an O, S, or N atom; specifically, a divalent fluorine-containing alcohol wherein the $R_F$ group is a polyfluoroalkylene group containing an O, S, or N atom and a terminal alcohol group, and having 5 to 160 carbon atoms, and A is an alkylene group having 1 to 3 carbon atoms, preferably 1 carbon atom. Examples thereof, for example, include a perfluoroalkylene ether diol represented by the general formula:

$$HO(CH_2)_fCF(CF_3)[OCF_2CF(CF_3)]_gO(CF_2)_hO[CF(CF_3)CF_2O]_iCF(CF_3)(CH_2)_fOH \quad [V]$$

f: 1 to 3, preferably 1
g+i: 0 to 50, preferably 2 to 50
h: 1 to 6, preferably 2

Among the hexafluoropropene oxide oligomer alcohols represented by the general formula [IV], a compound wherein m=1 and e=1 is described in Patent Document 7, and they are synthesized through the following step.

A fluorine-containing ether carboxylic acid alkyl ester represented by the general formula: $CF_3O[CF(CF_3)CF_2O]_nCF(CF_3)COOR$ (R: an alkyl group, n: an integer of 0 to 12) is subjected to a reduction reaction using a reducing agent such as sodium boron hydride.

Moreover, among the perfluoroalkylene ether diols represented by the general formula [V], a compound wherein f=1 is disclosed in Patent Documents 8 and 9, and they are synthesized via the following series of steps:

$$FOCRfCOF \rightarrow H_3COOCRfCOOCH_3 \rightarrow HOCH_2RfCH_2OH$$

Rf: $—CF(CF_3)[OCF_2C(CF_3)]_aO(CF_2)_cO[CF(CF_3)CF_2O]_bCF(CF_3)—$

The guest compound is generally a fluorescent compound, such as alizarin, alizarin red S, 2,3-dihydroxynaphthalene, diethoxydiphenylsilane, or diphenylsilanediol. In addition, the quest compounds include aliphatic alcohols, such as pentaerythritol, α-CD (cyclodextrin), β-CD (cyclodextrin), and γ-CD (cyclodextrin).

The proportion of these components is such that the boric acid is used at a ratio of about 0.01 to 10 parts by weight, preferably about 0.1 to 5 parts by weight, based on 100 parts by weight of the fluorine-containing alcohol, and such that the guest compound is generally used in an amount equimolar to the boric acid. When the amount of boric acid used is less than this range, water- and oil-repellency decreases. In contrast, when the amount of boric acid used is greater than this range, dispersibility in a solvent decreases. Moreover, when the amount of guest compound used is less than this range, dispersibility in a solvent decreases. In contrast, when the amount of guest compound used is greater than this range, water- and oil-repellency decreases.

The reaction between these components is performed under acidic or basic conditions. In the present Examples, the pH of the reaction solution becomes acidic by adding boric acid to a fluorine-containing alcohol. When they are reacted under basic conditions, an alkali metal hydroxide, such as KOH or NaOH, or an N-containing compound, such as $NH_3$, $NH_4OH$, triethylamine, or choline acid, is used.

The amount of the guest compound in the obtained fluorine-containing boric acid composite capsule particles is about 0.1 to 70 wt. %, preferably about 1 to 50 wt. %. The composite capsule particle size (measured by a dynamic light scattering method) is about 10 to 600 nm, preferably about 15 to 350 nm.

The FT-IR and UV absorption spectra of the fluorine-containing boric acid composite capsule particles, which are the reaction product, show the same peaks as those of the guest compound; therefore, it is considered that the guest molecule is clathrated or adsorbed, and encapsulated. The fluorine-containing boric acid composite capsule particles are formed as a reaction product of boric acid particles and both a fluorine-containing alcohol and a guest compound; however, other components may be mixed therein unless the object of the present invention is hindered.

EXAMPLES

The following describes the present invention with reference to Examples.

Example 1

1,100 mg (3.02 mmol) of $CF_3(CF_2)_5(CH_2)_2OH$ [FA-6], 50 mg (0.81 mmol) of boric acid, 200 mg (0.81 mmol) of alizarin, and 2.0 ml of tetrahydrofuran were changed in a 20-ml reaction vessel, and the mixture was stirred at room temperature for a day. Thereafter, the precipitate was removed by centrifugation, the solvent was distilled off, and drying was conducted, thereby obtaining 0.19 g of the target fluorine-containing boric acid composite capsule particles.

The resulting fluorine-containing boric acid composite capsule particles were measured for particle size (by a dynamic light scattering method), FT-IR, and UV. The FT-IR and UV absorption spectra showed the same peaks as those of the guest compound; therefore, it was considered that the guest molecule was clathrated or adsorbed, and encapsulated.

Examples 2 to 10

In Example 1, various guest compounds were used in place of alizarin.

The following table shows the results obtained in the above Examples.

TABLE

| Example | Guest compound Name | mg | mmol | Composite Amount (mg) | Yield (%) | Guest compound content (wt. %) |
|---|---|---|---|---|---|---|
| 1 | Alizarin | 194 | 0.81 | 188 | 14 | 14 |
| 2 | Alizarin red S | 277 | 0.81 | 29 | 2 | 19 |
| 3 | 2,3-Dihydroxy-naphthalene | 130 | 0.81 | 95 | 7.4 | 10 |
| 4 | Phenyl-trimethoxysilane | 160 | 0.81 | 212 | 16 | 12 |
| 5 | Diethoxy-diphenylsilane | 220 | 0.81 | 192 | 14 | 16 |
| 6 | Diphenylsilane-diol | 176 | 0.81 | 358 | 27 | 13 |
| 7 | Pentaerythritol | 110 | 0.81 | 139 | 11 | 9 |
| 8 | α-CD | 50 | 0.05 | 18 | 1.5 | 4 |
| 9 | β-CD | 50 | 0.04 | 23 | 1.9 | 4 |
| 10 | γ-CD | 50 | 0.04 | 23 | 1.9 | 4 |

The reaction products of Examples 1 to 7 were measured for FT-IR and UV-vis.
 FT-IR: A dry powder was measured by the KBr method using FT/IR-480 Plus (produced by JASCO Corporation)
 UV-vis: A dispersion of composite particles adjusting a concentration of 0.02 g/L with a 1,2-dichloroethane solution was measured in the visible light range using V-570 (produced by JASCO Corporation)

The invention claimed is:

1. Boric acid composite capsule particles containing fluorine comprising a condensate of a fluorinated alcohol, a guest compound, and boric acid particles, wherein the fluorinated alcohol is represented by the general formula:

$$R_F\text{-A-OH} \quad [I]$$

wherein $R_F$ is:
 a perfluoroalkyl group having 6 or less carbon atoms,
 a linear or branched perfluoroalkyl group containing a terminal perfluoroalkyl group having 6 or less carbon atoms and a perfluoroalkylene group having 6 or less carbon atoms, and containing an O, S, or N atom, or
 a polyfluoroalkyl group in which some of the fluorine atom or atoms of the perfluoroalkyl group are replaced by hydrogen atom or atoms, and which contains a terminal perfluoroalkyl group having 6 or less carbon atoms and a perfluoroalkylene group having 6 or less carbon atoms, wherein the perfluoroalkylene group may contain an O, S, or N atom, and one fluorine atom of the terminal perfluoroalkyl group may be replaced by —(CH$_2$)$_f$OH (wherein f is an integer of 1 to 3); and
 A is an alkylene group having 1 to 6 carbon atoms.

2. The boric acid composite capsule particles containing fluorine according to claim 1, wherein the fluorinated alcohol represented by the general formula [I] is a polyfluoroalkyl alcohol represented by the general formula:

$$CnF_{2n+1}(CH_2)_jOH \quad [II]$$

wherein n is an integer of 1 to 6, and j is an integer of 1 to 6.

3. The boric acid composite capsule particles containing fluorine according to claim 1, wherein the boric acid is used at a ratio of 0.01 to 10 parts by weight based on 100 parts by weight of the fluorinated alcohol, and the guest compound is used in an amount equimolar to the boric acid.

4. The boric acid composite capsule particles containing fluorine according to claim 1, wherein the amount of the guest compound in the fluorine-containing boric acid composite capsule particles is 0.1 to 70wt. %.

5. A surface-treating agent comprising the boric acid composite capsule particles containing fluorine according to claim 1 as an active ingredient.

6. The boric acid composite capsule particles containing fluorine according to claim 1, wherein the guest compound is a fluorescent compound.

7. The boric acid composite capsule particles containing fluorine according to claim 6, wherein the boric acid is used at a ratio of 0.01 to 10 parts by weight based on 100 parts by weight of the fluorinated alcohol, and the guest compound is used in an amount equimolar to the boric acid.

8. A method for producing boric acid composite capsule particles containing fluorine, the method comprising subjecting a fluorinated alcohol, a guest compound, and boric acid particles to a condensation reaction under acidic or alkaline conditions, wherein the fluorinated alcohol is represented by the general formula:

$$R_F\text{-A-OH} \quad [I]$$

wherein RF is:
 a perfluoroalkyl group having 6 or less carbon atoms,
 a linear or branched perfluoroalkyl group containing a terminal perfluoroalkyl group having 6 or less carbon atoms and a perfluoroalkylene group having 6 or less carbon atoms, and containing an O, S, or N atom, or
 a polyfluoroalkyl group in which some of the fluorine atom or atoms of the perfluoroalkyl group are replaced by hydrogen atom or atoms, and which contains a terminal perfluoroalkyl group having 6 or less carbon atoms and a perfluoroalkylene group having 6 or less carbon atoms, wherein the perfluoroalkylene group may contain an O, S, or N atom, and one fluorine atom of the terminal perfluoroalkyl group may be replaced by —(CH$_2$)$_f$OH (wherein f is an integer of 1 to 3); and
 A is an alkylene group having 1 to 6 carbon atoms.

* * * * *